United States Patent [19]

Duranel et al.

[11] Patent Number: 5,346,972
[45] Date of Patent: Sep. 13, 1994

[54] MAGNESIUM CHLORIDE PARTICLES WITH A TRUNCATED STRUCTURE, CATALYTIC COMPONENT SUPPORTED ON THESE PARTICLES, POLYOLEFINS OBTAINED BY EMPLOYING THIS CATALYTIC COMPONENT, PROCEDURES FOR MANUFACTURING THESE PRODUCTS

[75] Inventors: Laurent Duranel, Arthez de Bearn; Jean-Pierre Roche, Pau, both of France

[73] Assignee: Elf Atochem S. A., France

[21] Appl. No.: 968,036

[22] Filed: Oct. 26, 1992

Related U.S. Application Data

[62] Division of Ser. No. 657,756, Feb. 19, 1991, Pat. No. 5,212,133.

[30] Foreign Application Priority Data

Feb. 19, 1990 [FR] France ................ 90 01948

[51] Int. Cl.$^5$ ............ C08F 10/00; C08F 10/02; C08F 10/06
[52] U.S. Cl. .................... 526/125; 526/348; 526/348.6; 526/351; 526/352; 526/909
[58] Field of Search .................... 526/125, 351

[56] References Cited

U.S. PATENT DOCUMENTS

| | | | |
|---|---|---|---|
| 4,107,415 | 8/1978 | Giannini et al. | 526/125 |
| 4,742,138 | 5/1988 | Kaglyama | 526/125 |
| 4,762,898 | 8/1988 | Matsuura et al. | 526/125 |
| 4,851,208 | 7/1989 | Duranel et al. | 526/125 |
| 4,855,371 | 8/1989 | Job | 526/351 |
| 5,028,671 | 7/1991 | Kioka et al. | 526/125 |
| 5,137,996 | 8/1992 | Bailly et al. | 526/351 |

*Primary Examiner*—Edward J. Smith
*Attorney, Agent, or Firm*—John L. Sigalos

[57] ABSTRACT

Porous particles of $MgCl_2$ which have essentially the shape of two truncated right cones connected by their larger bases, which truncated cones are incurved towards the axis of symmetry perpendicular to the bases, at the intersection of the envelope of the truncated cones with two orthogonal planes passing through the said axis of symmetry. These particles are impregnated with a transition metal compound and employed as a catalytic component in the polymerization of olefins. The resultant polyolefins, especially polyethylene, polypropylene and their copolymers, are comprised of particles with a distinctive structure.

12 Claims, 5 Drawing Sheets

MAGNESIUM CHLORIDE PARTICLES WITH A TRUNCATED STRUCTURE, CATALYTIC COMPONENT SUPPORTED ON THESE PARTICLES, POLYOLEFINS OBTAINED BY EMPLOYING THIS CATALYTIC COMPONENT, PROCEDURES FOR MANUFACTURING THESE PRODUCTS

This application is a division, of application Ser. No. 07/657,756 filed Feb. 19, 1991, now U.S. Pat. No. 5,212,133.

BACKGROUND OF THE INVENTION

The present invention pertains to particles of magnesium chloride ($MgCl_2$) with a novel shape as well as to the procedure for manufacturing these particles. These $MgCl_2$ particles can be employed as a catalytic support, especially in the catalytic components of the Ziegler-Natta type. The polyolefins obtained by means of polymerization of olefins in the presence of the catalytic component containing this $MgCl_2$ also have a distinctive structure. These catalytic components and the polyolefins obtained in the presence of these components are also part of the invention.

SUMMARY OF THE INVENTION

When viewed under a microscope, the $MgCl_2$ in accordance with the invention is comprised of porous particles which have the shape of two truncated right cones connected by their larger bases, which truncated cones are incurved towards the axis of symmetry perpendicular to the bases, at the intersection of the envelope of the truncated cones with two orthogonal planes passing through the said axis of symmetry. The two truncated cones are generally essentially identical and symmetrical and such that the ratio D:h of the largest diameter "D" of the bases to the total height "h" of the two connected truncated cones is between 1 and 2, and more especially between 1.4 and 1.7. The usual D:d ratio of the largest diameter "D" of the particle to the largest diameter "d" of the small base of the truncated cones is between 2 and 4, and more especially between 2.5 and 3.5. The invention also comprises catalytic components embodying the $MgCl_2$ particles, polyoloefins obtained utilizing such catalytic components, and the process of making such products.

DETAILED DESCRIPTION

Figure 1:
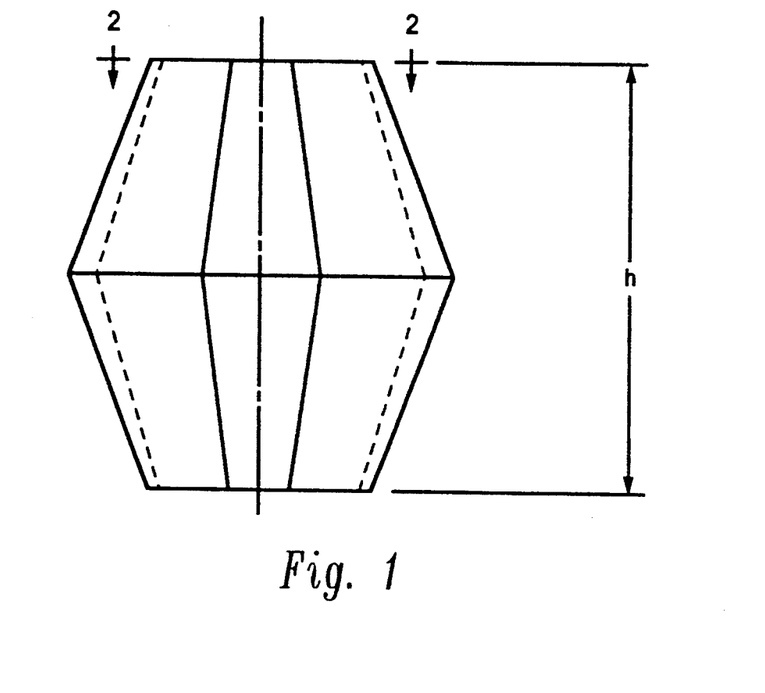
FIG. 1 is a schematic side view of a $MgCl_2$ particle in accord with the present invention.
Figure 2:
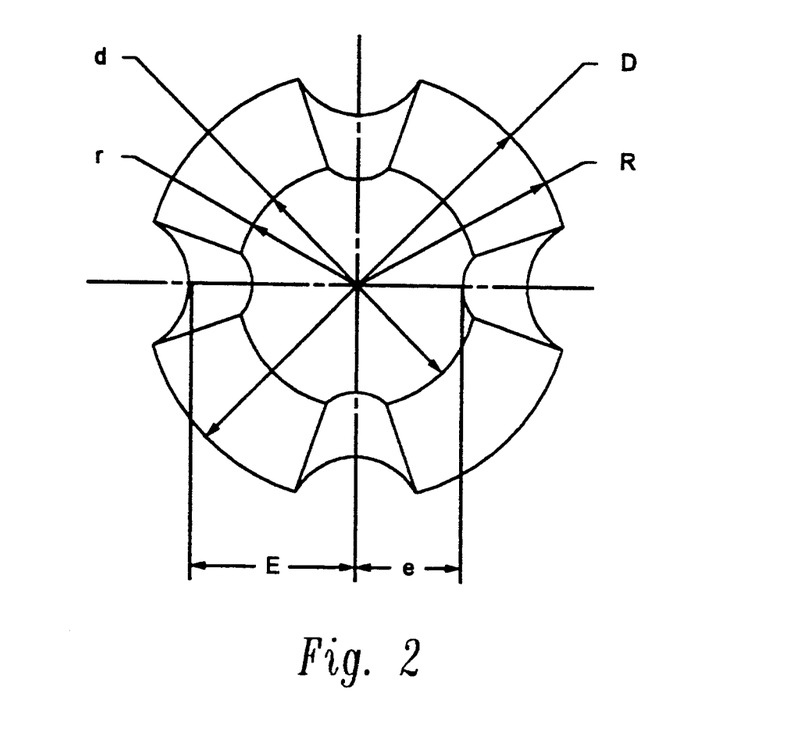
FIG. 2 is a top view taken along line 2—2 of FIG. 1.

The four incurvations on each of the two truncated cones, separated from each other essentially by 90°, referring to FIGS. 1 and 2, can be defined in relation to the largest radius "R" of the larger base of the truncated cones and to the distance "E" separating the center of this larger base of the truncated cone on this base from the point of maximum incurvation. This ratio R:E is generally between 1.1 and 1.5 and more especially between 1.2 and 1.4. These incurvations usually follow the two truncated cones from the larger base to the smaller base. Under these conditions, the ratio r:e can be between 1.1 and 1.5 and more especially between 1.2 and 1.4, "r" being the largest radius of one of the two smaller bases of the truncated cones and "e" representing the distance separating the center of this smaller base from the point of maximum incurvation on this same base.

These $MgCl_2$ particles have a rough and furrowed surface which assures excellent porosity. This porosity is generally between 0.5 and 3.5 $cm^3/g$, preferably between 1.5 and 2.5 $cm^3/g$; it can be estimated that in these particles the pores with radii between 5 and 100 nm represent up to 50% of the porous volume. Their specific surface area is usually between 100 and 400 $m^2/g$, preferably between 200 and 300 $m^2/g$.

The size of the $MgCl_2$ particles is generally between 10 and 100 $\mu$m, providing a narrow granulometric distribution. The D90:D10 range of granulometric distribution is usually lower than 4 and more generally lower than 3; D90 and D10 being the diameters smaller than which are 90% and 10% by weight of the particles, respectively.

These particles are obtained by precipitation with 1,4-dioxane of $MgCl_2$ in solution in alcohol, with the said solution being emulsified in a dispersant medium; the recovered $MgCl_2$ particles are then treated so as to totally eliminate the 1,4-dioxane.

The $MgCl_2$ to be treated is first put into solution in an alcohol under the usual dissolution conditions at a concentration equal to at most the limit of saturation at the temperature of the subsequent treatment of the solution. The alcohol employed is preferably a monoalcohol containing from 1 to 20 carbon atoms; n-butanol is the most highly recommended.

The solution of $MgCl_2$ in alcohol is emulsiifed in a dispersant medium, which is a liquid that is a nonsolvent of and inert in relation to the solution, at a temperature than can range from room temperature to 100° C. Although it is not necessary, the emulsion can be prepared in the presence of a surface-active agent, preferably a nonionic surface-active agent. The liquid dispersant is preferably selected from among the heavy hydrocarbons with at least eight carbon atoms in their molecule, such as the paraffin oils with a viscosity at 20° C. between 0.1 and 1 Pa.s. In the emulsion, the volume ratio of the dispersant medium to the alcohol phase, represented by the solution of $MgCl_2$ in alcohol, is usually between 1 and 5, preferably between 2 and 4.

As is known by the person skilled in this field, the agitation must be sufficient so as to maintain the alcohol phase in the form of droplets in the dispersant medium. As long as this condition is observed, the agitation conditions do not seem to be critical because, in particular, of a better stability of the emulsion at the procedure temperatures than at higher temperatures.

To this emulsion is added the precipitation agent which is 1,4-dioxane. The 1,4-dioxane is preferably added to the emulsion under agitation so as to assure immediate crystallization of the $MgCl_2$. The rate of introduction of the 1,4-dioxane does not appear to be critical; the 1,4-dioxane may be added as quickly as possible or allowed to flow slowly into the emulsion. The temperature of the 1,4-dioxane at the time of its introduction into the dispersion is also not critical. In contrast, so as to assure excellent precipation of $MgCl_2$, it is recommended that two volumes of 1,4-dioxane be employed per volume of alcohol solution and to avoid allowing the temperature of the reaction medium to drop below around 20° C.

The precipitated $MgCl_2$ is in the form of particles as previously defined. This $MgCl_2$ is recovered in the form of a $MgCl_2$, 1,4-dioxane complex containing generally on the order of 67% by weight of dioxane and 33% by weight of $MgCl_2$. This complex must be treated so as to totally eliminate the 1,4-dioxane from the $MgCl_2$. In fact, it is known that for certain applications of $MgCl_2$, the presence of 1,4-dioxane is harmful, particularly when $MgCl_2$ is employed as a support for a Ziegler-type catalytic component for polymerization; in fact, 1,4-dioxane has a catalyst-poisoning effect.

This dioxane can be eliminated from the $MgCl_2$ by any of the known means such as heating under vacuum for a sufficient length of time such as, for example, at 200°–208° C. under a vacuum between 1 and 2 kPa, or by hot fluidization of the complex at, for example, 400° C. under an inert gas stream.

A particularly noteworthy means of eliminating the 1,4-dioxane from the $MgCl_2$ is comprised of treating the complex obtained with an aluminum compound selected from among the nonhalogenated aluminoxanes, the nonhalogenated aluminosiloxanes or the $AlR_3$ alkylaluminums in which R represents an alkyl radical containing from 1 to 20 carbon atoms. The 1,4-dioxane removed from the $MgCl_2$ forms a complex with the aluminum compound. In order to achieve this, the $MgCl_2$ 1,4-dioxane complex is suspended in an inert liquid which is a solvent of the aluminum compound and the new complex formed: aluminum compound—1,4-dioxane after addition of the said aluminum complex. The inert liquid used for suspending the $MgCl_2$ complex can be, for example, selected from among the saturated or unsaturated hydrocarbons such as hexane, heptane, benzene, toluene, the partially or completely chlorinated compounds with a larger dipole moment such as $CH_2Cl_2, C_2H_4Cl_2, CCl_4, C_2Cl_4$ or orthodichlorobenzene, or from among the aromatic compounds having hydrocarbon groups and/or at least one chlorine atom. This treatment with the aluminum compound can be carried out under agitation at room temperature or under hot conditions, possibly under pressure so as to accelerate the reaction. The treatment temperature is not critical; this temperature is only limited by the boiling point of the inert liquid employed as a suspension agent. It is recommended that in the suspension an amount of aluminum compound be employed such that the molar ratio Al:1,4-dioxane be equal to or greater than 2. The excess of the aluminum is limited only by economic issues and the ease of washing. Rather than employing a large excess of the aluminum compound in the suspension, it is preferable for total elimination of the 1,4-dioxane to carry out multiple treatments of the $MgCl_2$ with the aluminum compound. After the usual washings and rinsings for elimination of the final traces of the complex of the aluminum compound and 1,4-dioxane and possibly drying, the $MgCl_2$ recovered is essentially pure and contains more than 24% by weight of Mg; it also preserves the previously defined shape and characteristics.

When the $MgCl_2$ particles are intended for use as a transition-metal support of Ziegler-Natta type catalytic components, it can be of value to not totally eliminate the aluminum compound which was used in the final treatment for eliminating the 1,4-dioxane.

X-ray observation of the $MgCl_2$ obtained shows a crystalline product with certain diffraction peaks, including the peak located at circa 0.181–0.184 nm (nanometer) that is characteristic of $MgCl_2$ as well as three additional peaks located at circa 0.75–0.85 nm, 0.70–0.75 nm and 0.50–0.52 nm. These measurements were carried out using PHILIPS equipment with the following characteristics:

* scatter band of 1°
* convergence aperture of 0.1°
* nickel filter
* normal focal tube made of copper
* PW 1130 generator
* PW 1050/25 goniometer
* acceleration voltage = 50 KV
* emission intensity = 30 mA
  goniometer rotation rate: 1°(2θ)/minute By means of its novel structure, the $MgCl_2$ obtained has all of the same advantages as $MgCl_2$ with a spherical shape, while reducing its drawbacks. In order to obtain good pourability, as measured in accordance with the standard ASTM D-1895, of the $MgCl_2$ and, more particularly, of the final polymer or copolymer, when the $MgCl_2$ is employed as a catalytic support, research was focused on the particle structures of $MgCl_2$. The spherical shape was particularly investigated in the case of catalysis such that the final polymer or copolymer particle, which essentially reproduces the support particle in a homothetic manner, would have this pourability quality. The disadvantage of this sphericity is that it facilitates the accumulation of electrostatic charges in the reactors and conduits, thereby causing, in particular, the adhesion of powder to the walls. The structure of the $MgCl_2$ in accordance with the invention makes it possible to reduce this type of disadvantage.

A Ziegler-type catalytic component can be obtained by combining the $MgCl_2$ in accordance with the invention with a transition metal compound. Thus, for example, this type of component can be obtained by deposition on the $MgCl_2$ of a titanium and/or vanadium compound which is preferably halogenated and, more specifically, of $TiCl_4$, $TiCl_3$, $VCl_4$, $VCl_3$ or $VOCl_3$. This catalytic compound combined with a cocatalyst selected from among the organometallic compounds of metals I to III on the Periodic Table and, more specifically, the aluminum compounds, is employed as a catalyst of the polymerization or copolymerication of linear or branched olefins such as ethylene, propylene, 1-butene, 1-hexene, 1-octene, 4-methyl-1-pentene, 1,3 butadiene and 1,9-decadiene.

At least one electron donor may be added during the preparation of the catalytic component and/or the cocatalyst. The electron donors may be selected, for example, from among the Lewis acids, the esters of oxygenated acids, the ketones, aldehydes, ethers, amines, amides, the silicon compounds such as the silanes, and the phosphorus compounds such as the phosphines and the phosphoramides; the preferred electron donors being the alkylated esters or polyesters of aromatic acids, the alkyl mono- or diethers, the alkoxysilanes and the alkylalkoxysilanes.

The catalyst obtained from a component prepared from the $MgCl_2$ of the invention is suitable for all types of polymerization of olefins: at high or low pressure, in suspension, in gas phase or mass polymerization.

The catalytic component obtained from the $MgCl_2$ in accordance with the invention is also comprised of particles which, when viewed under a microscope, have the shape essentially of two truncated right cones connected by their larger bases, which truncated cones are incurved towards the axis of symmetry perpendicular to the bases, at the intersection of the envelope of the truncated cones with two orthogonal planes passing through the said axis of symmetry. The two truncated cones are generally essentially identical and symmetrical such that the ratio D:H of the largest diameter "D" of the bases to the total height "h" of the two connected truncated cones is between 1 and 2 and, more especially, between 1.4 and 1.7. The usual ratio of the largest diameter "D" of the component particle to the largest diameter "d" of the small bases of the truncated cones is between 2 and 4 and, more especially, between 2.5 and 3.5. The four incurvations on each of the two truncated cones, separated from each other essentially by 90°, can be defined in relation to the largest radius "R" of the larger base of the truncated cones and to the distance "E" separating the center of this large base of the truncated cones from the point of maximum incurvation on this same base. This ratio R:E is generally between 1.1 and 1.5 and, more especially, between 1.2 and 1.4. These incurvations, which are much more accentuated at the large bases than at the small bases of the truncated cones, usually follow each truncated cone from the larger base to the smaller base. Under these condition, the ratio r:e can be between 1.1 and 1.5 and, more especially, between 1.2 and 1.4, with "r" being the largest radius of one of the two small bases of the truncated cones and "e" representing the distance separating the center of this small base from the point of maximum incurvation on this same base.

These catalytic component particles have an essentially smooth surface; the porosity of these particles is generally between 1 and 3 $cm^3/g$ and, preferably, between 1.5 and 2.5 $cm^3/g$. Their specific surface area is usually between 100 and 400 $m^2/g$ and, preferably, between 200 and 300 $m^2/g$.

The size of the catalytic component particles is generally between 4 and 100 $\mu m$ for a narrow granulometric distribution. The D90:D10 range of granulometric distribution, as previously defined, is usually lower than 4 and more generally lower than 3.

The catalytic component can advantageously be prepared by impregnation, in a known manner, of the previously described $MgCl_2$ particles by a transition metal compound which is liquid or in solution and which has one or more halogen atoms, particularly chlorine atoms. Prior to this impregnation or at least at the same time, it can be advisable to carry out the deposition of at least one organic compound selected from among the previously mentioned electron donors.

The resultant catalytic composition, combined with a conventional cocatalyst, usually selected from among the organoaluminum compounds such as the aluminoxanes, the aluminosiloxanes, the compounds with Al-R-Al bonds in whch R represents an alkyl group, or of formula $AlX_qR's$ in which X represents Cl or OR' with R' designating a $C_1$ to $C_{16}$, preferably a $C_1$ to $C_{12}$, alkyl radical while q and s are numbers such that $1<s<3$, $0<q<2$ with $q+s=3$, form a catalyst which is suitable for the polymerization of olefins and, more specifically, of ethylene, propylene, 1-butene, 4-methyl-1-pentene and 1-hexene or their mixtures. The possibility is not excluded of combining with the cocatalyst an electron donor such as previously defined. The catalytic component and the cocatalyst are combined in proportions such that the molar ratio of the aluminum contained in the cocatalyst to the transition metal of the said component is between 0.5 and 1000, preferably between 1 and 400.

The polymerization of the previously mentioned olefins or, in general, $C_2$ to $C_{12}$ olefins singly or in mixtures, by means of the previously defined catalytic system can be implemented in solution or in suspension in an inert liquid medium and notably in an aliphatic hydrocarbon such as n-heptane, n-hexane, isohexane, isobutane or mass polymerization can be carried out in at least one of the olefins to be polymerized which is maintained in the liquid or hypercritical state.

The operating conditions, notably the temperatures, pressures, amounts of catalytic system, for these liquid-phase polymerizations are those which are usually recommended for the similar cases involving supported or unsupported conventional catalytic systems of the Ziegler-Natta type.

For example, for polymerization carried out in suspension or in solution in an inert liquid medium, one can operate at temperatures up to 250° C. and under pressures ranging from atmospheric pressure to 250 bar. In the case of polymerization in a liquid propylene medium, the temperatures can go as high as the critical temperature and the pressures can be between atmospheric pressure and the critical pressure. For mass polymerization or mass copolymerization of ethylene leading to polyethylenes or to a predominately ethylene-containing copoylmers, one can operate at temperatures between 130° and 350° C. and a pressures randing from 200 to 3500 bar.

The catalytic system obtained by combination of the transition metal component according to the invention witha a cocatalyst and possibly an electron donor as previously defined, can also be used for the gas-phase polymerization of the previously mentioned olefins or olefins mixtures. Specifically, gas-phase polymerization can be carried out with contact of the said catalytic system with a mixture of ethylene or propylene and one or more $C_2$ to $C_{12}$ olefins such as ethylene, propylene, 1-butene, 1-hexene, 4-methyl-1-pentene and 1-octene, which contains when it is in contact with the catalytic system a molar proportion of $C_2$ to $C_{12}$ comonomers between 0.1 and 90%, preferably between 1 and 60%.

The gas-phase polymerization of the olefin or olefins in contact with the catalytic system can be carried out in any reactor that allows gas-phase polymerization, particularly in an agitated and/or fluided bed reactor. The implementation conditions for the gas-phase polymerization notably temperature, pressure, injection of the olefin or olefins into the agitated and/or fluidized bed reactor, control of the polymerization temperature and pressure, are similar to those recommended in the prior art for the gas-phase polymerization of olefins. Operations are generally carried out at a temperature below the melting point Tf of the polymer or copolymer to be synthesized, more specifically between +20° C. and (Tf−5)°C., and under a pressure such that the olefin or olefins, and possibly the other hydrocarbon monomers present in the reactor, are essentially in vapor phase.

The solution, suspension, mass, or gas-phase polymerization can be carried out in the presence of a chain-transfer agent so as to control the melt-flow index of the polymer or copolymer to be produced. The preferred chain-transfer agent is hydrogen which is used in an amount which can be as high as 90%, preferably between 0.1 and 60%, of the total volume of the olefins and hydrogen brought into the reactor.

The transition metal component in accordance with the invention can also be used for the preparation of an active prepolymer, which can be used alone or in combination with a cocatalyst selected from the previously defined aluminum compounds.

The said active prepolymer is obtained by bringing into contact one or more $C_2$ to $C_{12}$ alpha-olefins with a catalytic system formed by combining the transition metal component according to the invention with a cocatalyst selected from among the compounds that were previously mentioned for this purpose and employed in the previously specified proportions, with the said $C_2$ to $C_{12}$ olefin or olefins being used in an amount representing 2 to 500 grams, perferably 2 to 100 grams, of $C_2$ to $C_{12}$ olefin or olefins per gram of the transition metal component.

The catalytic component in accordance with the invention is particularly valuable in the polymerization or copolymerization of ethylene or propylene or their mixtures with each other or with another olefin in that it makes it possible to obtain polymers or copolymers with novel structures to the extent, obviously, that the polymerization temperature is lower than the melting point of the polymer formed.

When viewed under a microscope, the polyethylene or the copolymers of ethylene generally with more than 80% by weight of ethylene and at least one other olefin, usually a $C_3$ to $C_{12}$ olefin, have the appearance of particles which are pierced centrally and comprised of a succession of agglometrates attached to each other and arranged in a ring-like manner. These particles have an average size hewteen 300 and 1000 μm and are comprised of agglomerates of a size generally between 50 and 400 μm, more specifically between 200 and 2000 μm. The polymer or copolymer obtained, which has a narrow granulometric distribution usually between 3 and 4, has a high apparent density, measured according to the standard ASTM D1895 Method A, benerally between 0.35 and 0.40 g/cm³. The pourability of the powders is also high with values that are usually lower than or equal to 20 seconds, according to the standard ASTM D1895.

When viewed under a microscope, the polypropylene or the copolymers of propylene and ethylene or at least one other $C_4$ to $C_{12}$ olefin, generally with more than 80% by weight of propylene, have the form of particles comprised of two truncated right cones connected by their larges bases, which truncated cones are incurred towards the axis of symmetry perpendicular to the bases, at the intersection of the envelope of the truncated cones with two orthogonal planes passing through the said axis of symmetry. The two truncated cones are generally essentially identical and symmetrical and such that the ratio D:h of the largest diameter "D" of the bases to the total height "h" of the two connected truncated cones is between 1 and 2, more specifically between 1.4 and 1.7. The usual ratio D:d of the largest diameter "D" of the particle to the largest diameter "d" of the small bases of the truncated cones is between 2 and 4, more specifically between 2.5 and 3.5. The four incurvations on each of the two truncated cones, separated from each other essentially by 90%, can be defined in relation to the largest radius "R" of the larger base of the truncated cone and to the distance "E" separating the center of this larger base of the truncated cones from the point of maximum incurvation on this same base. This ratio R:E is generally between 1.1 and 1.5, more specifically between 1.2 and 1.4. These incurvations usually follow the two truncated cones from the larger base to the smaller base. Under these conditions, the ratio r:e can be between 1.1 and 1.5, more specifically between 1.2 and 1.4, with "r" being the smallest radius of one of the two small bases of the truncated cones and "e" representing the distance separating the center of this small base from the point of maximum incurvation on this same base. Attached FIGS. 1 and 2 show a front view and a top view of and are representative of this polypropylene and its copolymers.

These propylene and propylene copolymer particles, the size of which is generally between 200 and 500 μm for a narrow granulometric distribution, have a specific surface area between 0.1 and 3 m2/g. The D90:D10 range of granulometric distribution is usually lower than 4, more generally lower than 3. The apparent densities of the propylene polymers or copolymers are particularly high and generally between 0.45 and 0.55 g/cm³. The pourability of the powders is usually between 20 and 25 seconds.

The particles of polypropylene and its copolymers obtained from a $MgCl_2$ component and/or support as previously described are generally essentially homothetic to the particles of the $MgCl_2$ component and/or support.

The D90:D10 range of granulometric distribution is determined by means of a MALVERN 1600 laser granulometer. The specific surface area is measured by isothermal physical absorption of nitrogen at the temperature of liquid nitrogen, BET method, on a QUANTASORB device. The porous volume is determined by intrusion of mercury under pressure with an ERBA-SCIENCE 1500 porosimeter.

The following examples illustrate the invention without, however, limiting it.

Example 1

Figure 3:
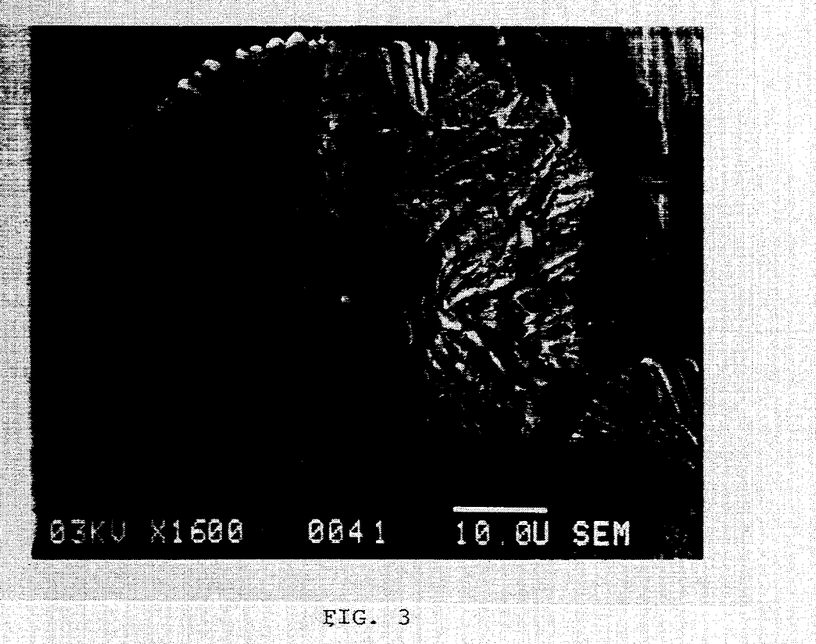
FIG. 3 is a photomicrograph (1600×) of a $MgCl_2$ particle in accord with the present invention.
Figure 4:
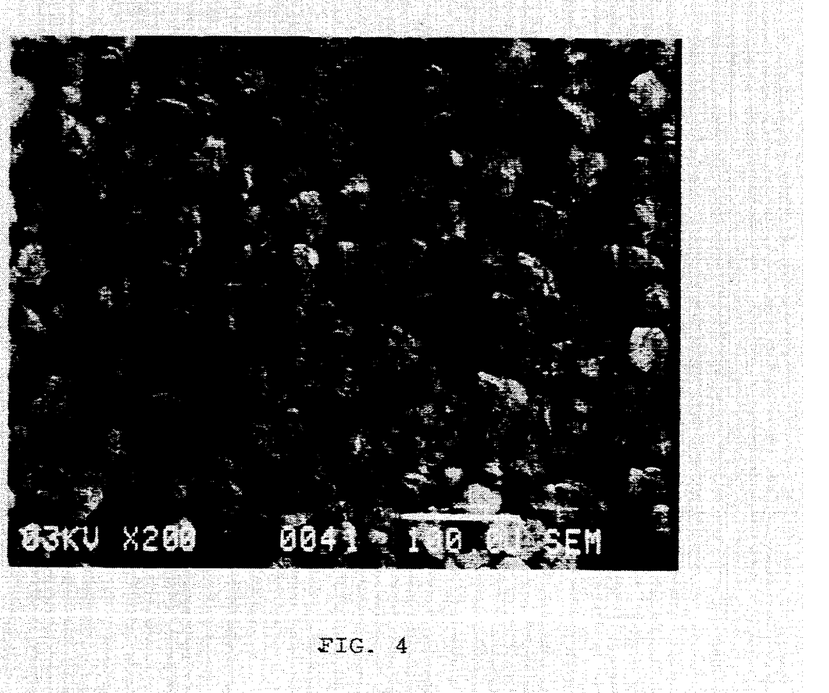
FIG. 4 is a photomicrograph (200×) of a group of $MgCl_2$ particles in accord with the present invention.

Into an agitated reactor thermostated at 40° C. and purged with dry nitrogen are introduced 50 mL of a solution of $MgCl_2$ in n-butanol such that the BuOH:$MgCl_2$ molar ratio is 10. One then adds 200 mL of a paraffin oil with a viscosity of 0.2 Pa.s measured at 20° C. Agitation is brought to a speed such that the linear speed at the end of a blade is 120 m/s. The biphasic mixture is left under agitation for 5 minutes and then 125 mL of 1,4-dioxane is added quickly and all at once. Precipitation of the $MgCl_2$, 1,4-dioxane complex is immediate. After filtration, washing with hexane and drying under a nitrogen stream, one recovers circa 14 g of a white pulverized powder with very good pourability, the particles of which have a morphology corresponding to FIGS. 3 and 4. The composition of the solid prepared in this manner is 67% 1,4-dioxane and 33% $MgCl_2$. The average largest diameter of the particles is 27 $\mu m$ and the D90:D10 ratio is 3.6. The specific surface area measured by. BET is 4 $m^2/g$ and the porosity is 1.1 $cm^3/g$.

5.8 g of this composition is treated with a solution of triethylaluminum in 1,2-dichloroethane such that the Al:1,4-dioxane molar ratio is 2 and the concentration in aluminum is 1 mole per liter. After filtration, washing and drying of the solid, one obtains a powder at least 80% of the structure of which corresponds to that in FIGS. 3 and 4. The mean diameter of the particles is 15 $\mu m$. The porosity is 2.16 $cm^3/g$ for a specific surface area of 272 $m^2/g$, the mean D:h ratio=1.5 and the D:d ratio=2.5 with R:E=1.2 and r:e=1.2. The D90:D10 ratio=3.5. The $MgCl_2$ contains 24.5% Mg.

Figure 5:
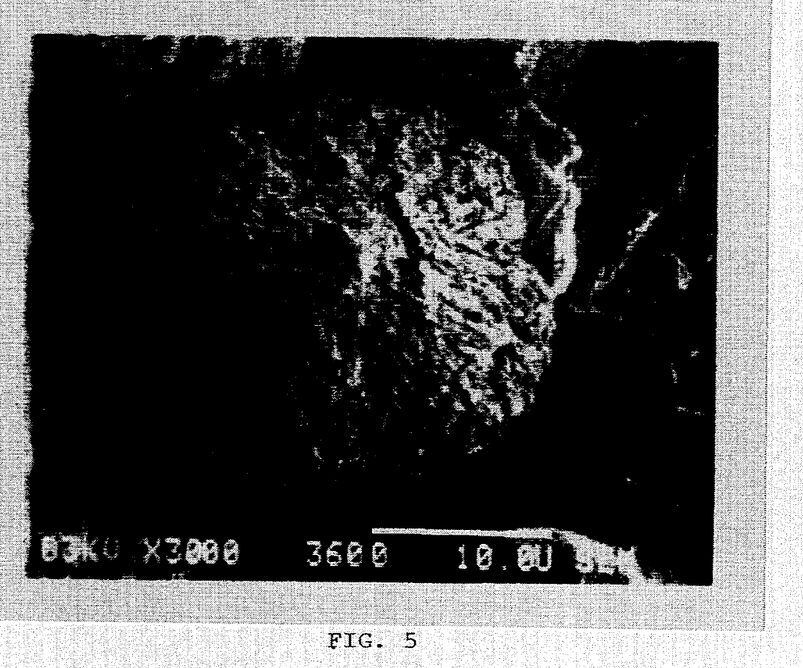
FIG. 5 is a photomicrograph (3000×) of a catalytic component particle in accord with the present invention.
Figure 6:
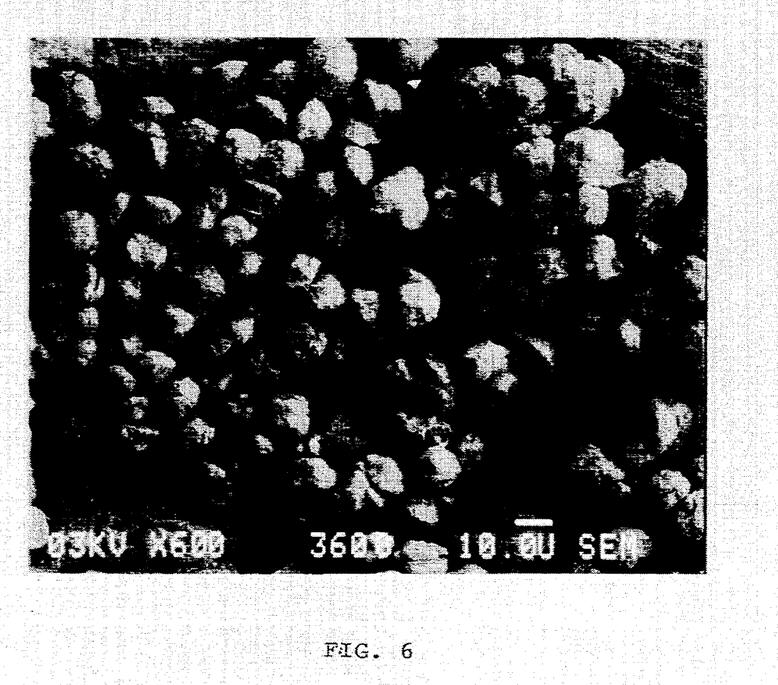
FIG. 6 is a photomicrograph (600×) enlargement of a group of catalytic component particles in accord with the present invention.

This powder is taken up in 50 mL of a solution of dioctyl phthalate in 1,2-dichloroethane at 0.2 mole for 2 hours at 80° C. After filtration, 50 mL of pure $TiCl_4$ is added to the $MgCl_2$. After 2 hours under agitation at 80° C., a new filtration is carried out and the solid is taken up in 50 mL of a solution of 1,2-dichloroethane containing 1 mole of $TiCl_4$ for 30 minutes at 80° C. under agitation. After filtration, this treatment with dilute $TiCl_4$ is carried out again. After filtration, washing with hexane and drying, one obtains 1.9 g of catalytic component containing 69%, 23.8% and 0.9% by weight of chlorine, magnesium and titanium, respectively. The structure of the component particles obtained corresponds to those of FIGS. 5 and 6. The mean diameter of the particles is 15 $\mu m$ and the range of the granulometric distribution is 3.4. On average, the particles have the following characteristics: D:h=1.5, D:d=2.5, R:E=1.2 and r:e=1.2. Their mean porosity is 2.2 $cm^3/g$ for a specific surface area of 290 $m^2/g$.

Into a stainless steel reactor are introduced 1.2 L of hydrogen, 600 g of liquid propylene, 1.3 g of triethylaluminum and 0.1 molar equivalent in relation to the aluminum of cyclohexylmethyldimethoxysilane. 20 mg of the prior catalytic component is added. The reactor is kept under agitation for 1 hour at 70° C.

Figure 8:
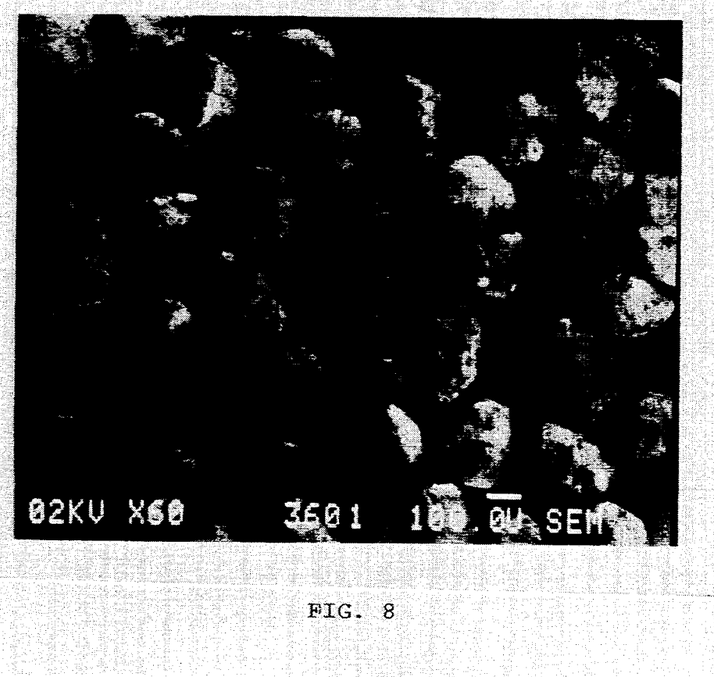
FIG. 8 is a photomicrograph (60×) of a group of polypropylene particles in accord with the present invention.

One-recovers 172 g of polypropylene with good pourability, the structure of the particles of which corresponds to that shown in FIG. 8. The mean diameter of the polymer particles is 270 $\mu m$ and the range of granulometric distribution is 2.6. The level of fine particles smaller than 100 $\mu m$ is 0.2%. The apparent density is 0.46 $g/cm^3$ and the pourability is 21 seconds. The level of polymer insoluble in boiling heptane is 95.1%. The melt-flow index measured according to the standard ASTM D1238 Method L is 4.

Example 2

A $MgCl_2$ powder is prepared under the conditions of Example 1 except that the operation is carried out at 65° C. rather than 40° C. 14 g of powder is finally obtained and treated with a solution of triethylaluminum in 1,2-dichloroethane under the same conditions as in Example 1. The final structure of the particles corresponds to that shown in FIGS. 3 and 4. The mean diameter of the particles is 35 m and the range of their granulometric distribution is 3.8. The porosity=1.7 $cm^3/g$, the specific surface area=229 $m^2/g$, D:h=1.6, D:d=3, R:E=1.3, r:e=1.3, Mg=24.3%. The powder obtained is put into suspension in 50 mL of pure $TiCl_4$ for 3 hours at 80° C. After filtration, washing with hexane and drying, the catalytic component obtained contains 23.5%, 1.4% and 71.3% by weight of magnesium, titanium and chlorine, respectively. The structure of the particles of the resultant component corresponds to that of FIGS. 5 and 6. The mean diameter of the particles is 30 $\mu m$ and the range of the granulometric distribution is 3.3. On average the particles have the following characteristics: D:h=1.6, D:d=3, R:E=1.3, and r:e=1.3. Their mean porosity is 1.53 $cm^3/g$ for a specific surface area of 207 $m^2/g$.

Figure 9:
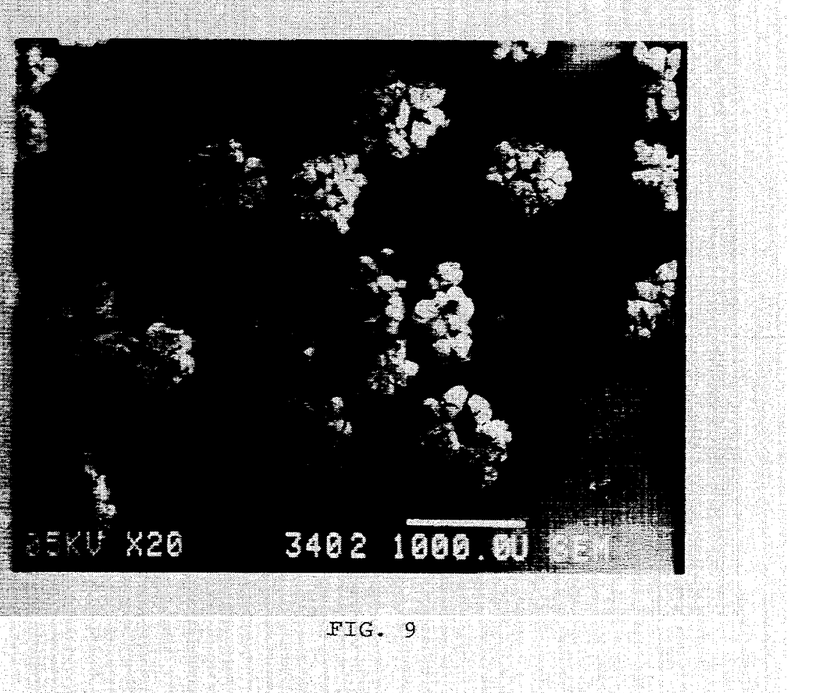
FIG. 9 is a photomicrograph (20×) of a group of ethylene-1-butene copoylmer particles in accord with the present invention.

Into a stainless steel reactor, one introduces under nitrogen 2 liters of hexane, 10 mM of triisobutylaluminum and 10 mg of the preceding catalytic component. The temperature is brought to 86° C. The reaction medium is put under a pressure of 0.4 MPa of hydrogen. The reactor is fed with a mixture of ethylene and of 1-butene at 1% 1-butene. The monomer pressure is 0.6 MPa. After three hours of reaction, one recovers 173 g of ethylene-butene copolymer with very good pourability, the structure of the particles of which corresponds to that shown in FIG. 9. The mean diameter of the polymer particles is 500 $\mu m$ and the range of granulometric distribution is 3.8. The apparent density is 0.35 $g/cm^3$ and the pourability is 19 seconds. The melt-flow indices measured according to the standard ASTM D1238 Methods E and F are 1 and 34, respectively.

Example 3

With all other conditions corresponding to those of Example 1, 240 mL of butanol solution of $MgCl_2$ and 1150 mL of paraffin oil are employed. The linear agitation speed at the end of the blade is 280 m/s and the operating temperature is 90° C. 700 mL of 1,4-dioxane is added. One obtains 66 g of powder, the structure of the particles of which correspons to that shown in FIGS. 3 and 4. The mean diameter of the particles is 15 $\mu m$ and the range of granulometric distribution is 3.5. The porosity=2.1 $Cm^3/g$ the specific surface area=217 $m^2/g$, D:h=1.5, D:d=3, R:E=1.2 and r:e=1.2

Example 4

Use is again made of the catalytic component as described in Example 2.

Figure 7:
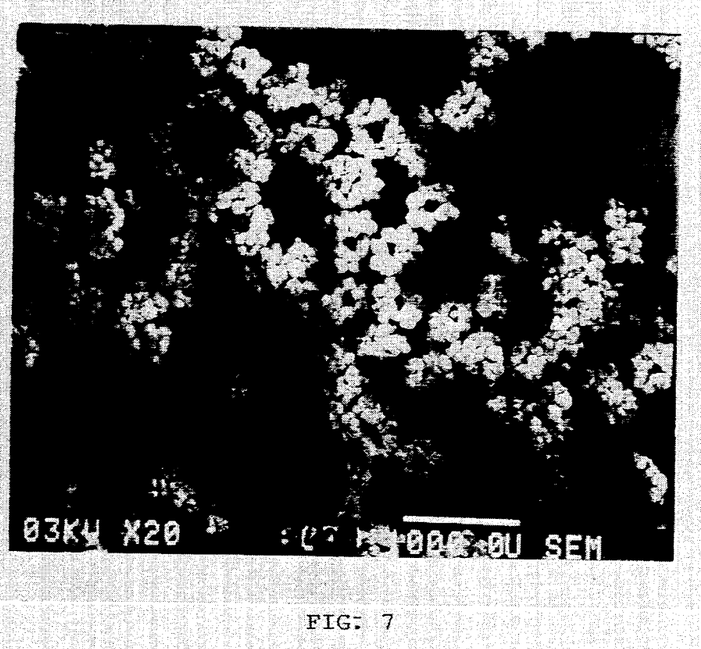
FIG. 7 is a photomicrograph (20×) of a group of polyethylene particles in accord with the present invention.

The homopolymerization of ethylene is carried out under the same conditions as those of Example 2, except with regard to the partial pressures of hydrogen and ethylene which are 0.47 MPa and 0.63 MPa, respectively. After 2 hours of reaction, 53 g of polyethylene are recovered. The structure of the particles corresponds to that shown in FIG. 7.

The mean diameter is 640 microns. The range of granulometric distribution is 3.4. The apparent density is 0.37 $g/cm^3$ and the pourability is 20 seconds.

The melt-flow indices measured according to the standard ASTM D1238 Methods E and F are 3.5 and 108, respectively.

Example 5

The catalytic component described in Example 1 is employed in the copolymerization of propylene and ethylene. Into a stainless steel reactor purged with nitrogen are introduced in order: 1.2 liters of hydrogen, 600 g of liquid propylene, 1.3 g of triethylaluminum and 0.1 molar equivalent in relation to the aluminum of cyclohexylmethyldimethoxysilane. Twenty mg of the catalytic component is then added and the temperature is raised to 70° C.

As soon as the reaction temperature reaches 70° C., ethylene at a flow rate of 10 Nl/min is introduced into the reactor for 1 hour.

After degassing the reactor, 160 g of propylene-ethylene copolymer is recovered.

Figure 10:
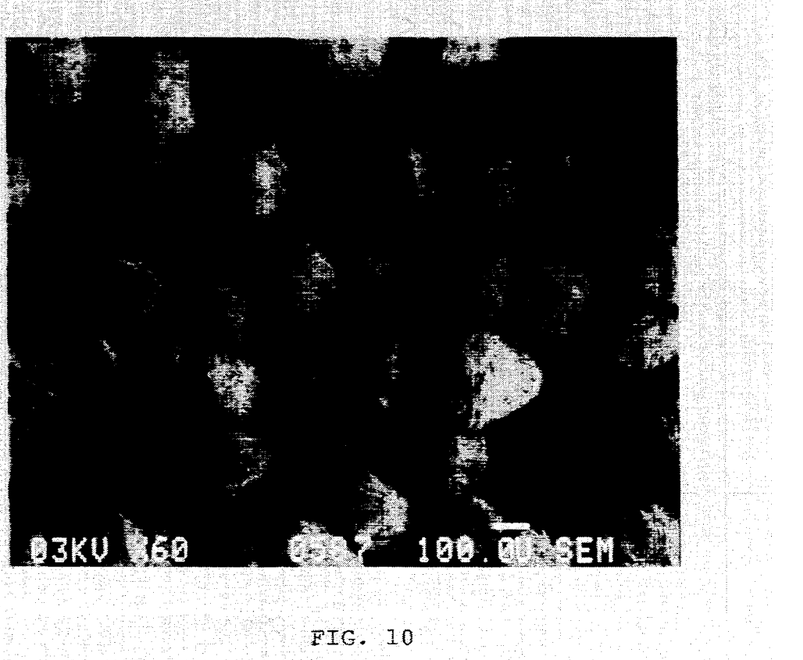
FIG. 10 is a photomicrograph (60×) of a group of propylene-ethylene copolymer particles in accord with the present invention.

The structure of the particles corresponds to that of FIG. 10. The mean diameter is 330 μm and the range of granulometric distribution is 3.6. The level of fine particles smaller than 100 μm is 1%.

The apparent density is 0.43 g/cm$^3$ and the pourability is 25 seconds.

The melt-flow index of the copolymer measured according to the standard ASTM D1238 Method L is 2.5. The level of copolymer insoluble in boiling heptane is 82%. Infrared analysis of the level of ethylene in the copolymer yielded a value of 3.5% by weight.

While the invention has been described in connection with a preferred embodiment, it is not intended to limit the scope of the invention to the particular form set forth, but on the contrary, it is intended to cover such alternatives, modifications, and equivalents as may be included with the spirit of the invention as defined by the appended claims.

What is claimed is:

1. A polyolefin obtained by polymerization of one or more $C_2$ to $C_{12}$ olefins in the presence of a catalytic system comprising a catalytic component containing $MgCl_2$ and a transition metal compound, and of a cocatalyst based on an organoaluminum compound, wherein said polyolefin consists of particles having essentially the shape of two truncated right cones connected by their larger bases, which truncated cones are incurved towards the axis of symmetry perpendicular to the bases, at the intersection of the envelope of the truncated cones with two orthogonal planes passing through said axis of symmetry.

2. The polyolefin of claim 1, wherein the polyolefin is a polyethylene or copolymer of ethylene and at least one other $C_3$ to $C_{12}$ olefin and which has the form of particles pierced in their center and constituted of a succession of agglomerates attached to each other and arranged in a ring.

3. The polyethylene of claim 2, wherein the mean size of the particles is between 300 and 100 μm and that of the agglomerates is between 50 and 300 μm.

4. The polyolefin of claim 1, wherein the polyolefin is a polypropylene or copolymer of propylene at more than 80% by weight of propylene and balance ethylene or another $C_4$ to $C_{12}$ olefin.

5. The polypropylene or copolymer of propylene of claim 4, wherein the two truncated cones of each particle are essentially identical and symmetrical.

6. The polypropylene or copolymer of propylene of claim 5, wherein in the particles the ratio D:h of the largest diameter "D" of the bases to the total height "h" of the two connected truncated cones is between 1 and 2.

7. The polypropylene or copolymer of propylene of claim 6, wherein in the particles the ratio D:d of the largest diameter "D" of the particle to the largest diameter "d" of the small bases of the truncated cones is between 2 and 4.

8. The polypropylene or copylymer of propylene of claim 7, wherein in the particles the four incurvations are separated from each other essentially by 90°.

9. The polypropylene or copolymer of propylene of claim 8, wherein in the particles the ratio R:E of the laragest radius "R" of the larger base of the truncated cones to the distance "E" separating the center of this larger base from the point of maximum incurvation on this same base is between 1.1 and 1.5.

10. The polypropylene or copymer of propylene of claim 9, wherein in the particles the ratio r:e of the largest radius "r" of one of the two small bases of the truncated cones to the distance "e" separating the center of this small base from the point of maximum incurvation on this same base is between 1.1 and 1.5.

11. The polypropylene or copolymer of propylene of claim 10, wherein its specific surface area is between 0.1 and 3 m$^2$/g.

12. The polypropylene or copolymer of propylene of claim 11, wherein the size of the particles is between 200 and 500 μm with a D90:D10 range of granulometric distribution lower than 4.

* * * * *

UNITED STATES PATENT AND TRADEMARK OFFICE
CERTIFICATE OF CORRECTION

PATENT NO. : 5,346,972
DATED : September 13, 1994
INVENTOR(S) : Laurent Duranel et al It is certified that error appears in the above-indentified patent and that said Letters Patent is hereby corrected as shown below:

Column 12, line 2, "100" should read --1,000--.

Signed and Sealed this

First Day of November, 1994

Attest:

BRUCE LEHMAN

*Attesting Officer*     *Commissioner of Patents and Trademarks*